United States Patent
Okamoto et al.

(10) Patent No.: US 10,843,988 B2
(45) Date of Patent: Nov. 24, 2020

(54) METHOD FOR PRODUCING 1-CHLORO-3,3,3-TRIFLUOROPROPENE

(71) Applicant: CENTRAL GLASS COMPANY, LIMITED, Yamaguchi (JP)

(72) Inventors: Masamune Okamoto, Saitama (JP); Satoru Okamoto, Saitama (JP)

(73) Assignee: CENTRAL GLASS COMPANY, LIMITED, Yamaguchi (JP)

(*) Notice: Subject to any disclaimer, the term of this patent is extended or adjusted under 35 U.S.C. 154(b) by 0 days.

(21) Appl. No.: 16/571,403

(22) Filed: Sep. 16, 2019

(65) Prior Publication Data

US 2020/0024218 A1 Jan. 23, 2020

Related U.S. Application Data

(63) Continuation of application No. PCT/JP2018/021821, filed on Jun. 7, 2018.

(30) Foreign Application Priority Data

Jun. 30, 2017 (JP) ................. 2017-128293

(51) Int. Cl.
    *C07C 17/20* (2006.01)
    *C07C 21/18* (2006.01)
    *C07C 17/25* (2006.01)

(52) U.S. Cl.
    CPC ............ *C07C 17/202* (2013.01); *C07C 17/25* (2013.01); *C07C 21/18* (2013.01)

(58) Field of Classification Search
None
See application file for complete search history.

(56) References Cited

U.S. PATENT DOCUMENTS

| | | | |
|---|---|---|---|
| 2012/0059199 A1 | 3/2012 | Pokrovski et al. | |
| 2012/0271069 A1 | 10/2012 | Wang et al. | |
| 2014/0249336 A1 | 9/2014 | Komatsu et al. | |
| 2015/0011806 A1* | 1/2015 | Hibino | C07C 17/25 570/156 |
| 2015/0148571 A1 | 5/2015 | Chaki et al. | |
| 2016/0355453 A1 | 12/2016 | Ohkubo et al. | |
| 2017/0113986 A1* | 4/2017 | Okamoto | C07C 17/206 |
| 2019/0031583 A1 | 1/2019 | Okamoto et al. | |

FOREIGN PATENT DOCUMENTS

| | | |
|---|---|---|
| JP | H10-67693 A | 3/1998 |
| JP | 2013-538809 A | 10/2013 |
| JP | 2014-520070 A | 8/2014 |
| JP | 2014-530233 A | 11/2014 |
| JP | 2015-525201 A | 9/2015 |
| JP | 2016-222619 A | 12/2016 |
| JP | 2017-124997 A | 7/2017 |
| WO | 2016/009946 A1 | 1/2016 |
| WO | 2016/182715 A1 | 11/2016 |

OTHER PUBLICATIONS

International Search Report and Written Opinion of the International Searching Authority dated Jul. 24, 2018 for the PCT application No. PCT/JP20181021821, With English translation of the International Search Report.

Written Opinion of the International Searching Authority (PCT/ISA/237) dated Jul. 24, 2018 for the PCT application No. PCT/JP2018/021821.

Office Action issued in corresponding Japanese Patent Application No. 2019-526757 dated May 26, 2020, along with a partial machine translation.

\* cited by examiner

*Primary Examiner* — Medhanit W Bahta
(74) *Attorney, Agent, or Firm* — Hauptman Ham, LLP

(57) ABSTRACT

A method for manufacturing 1-chloro-3,3,3-trifluoropropene (1230zd) is provided. The method includes contacting a halogenated hydrocarbon compound having a carbon number of 3 and represented by a general formula (1) with a metal catalyst in a gas phase.

$$CF_aCl_{3-a}\text{---}CH_2\text{---}CHF_bCl_{2-b} \quad (1)$$

In the formula, a is an integer from 0 to 2, b is 1 or 2 when a=0, b is 0 or 1 when a=1, and b is 0 when a=2.

11 Claims, No Drawings

METHOD FOR PRODUCING 1-CHLORO-3,3,3-TRIFLUOROPROPENE

CROSS REFERENCE TO RELATED APPLICATION

This application is based upon and claims the benefit of priority from the prior Japanese Patent Application No. 2017-128293, filed on Jun. 30, 2017. Further, this application is a continuation of International Application No. PCT/JP2018/021821, filed on Jun. 7, 2018. Both of the priority documents are hereby incorporated by reference in their entireties.

FIELD

An embodiment of the present invention relates to a manufacturing method of 1-chloro-3,3,3-trifluoropropene (hereinafter, also referred to as 1233zd).

BACKGROUND

1233zd is a known compound and has been widely employed in a variety of usages due to its low global warming potential coefficient (GWP).

A variety of methods has been known for manufacturing 1233zd. For example, a method including fluorination of 1,1,3,3,3-pentachloropropane (hereinafter, also referred to as 240fa) in a gas phase in the presence of hydrogen fluoride is known (Japanese Patent Application Publication No. H10-067693). A method is also known where a product obtained by the reaction of 240fa with hydrogen fluoride, such as 1,3,3-trichloro-1,1-difluoropropane (hereinafter, also referred to as 242fa), is fluorinated with hydrogen fluoride in a gas phase in the presence of chlorine (International Patent Application Publication No. 2016/009946). Although 1233zd can be obtained in a high yield by each method, a more than stoichiometric amount of hydrogen fluoride is required. The use of a large amount of hydrogen fluoride increases the risk of an accident resulting in injury or death and puts pressure on risk management when leaked.

An industrially applicable manufacturing method for manufacturing 1233zd is still being demanded.

SUMMARY

An object of an embodiment of the present invention is to provide an efficient (and industrially applicable) manufacturing method of 1-chloro-3,3,3-trifluoropropene (1233zd).

Diligent study was made by the inventors to solve the aforementioned problem. As a result, it was found that 1233zd can be manufactured by allowing a halogenated hydrocarbon compound having a carbon number of 3 to contact with a metal catalyst in a gas phase, especially, with a metal catalyst in a gas phase in the presence of a fluorocarbon compound, through which the present invention was made. The present invention is realized by the embodiments described below.

Namely, an embodiment of the present invention is a manufacturing method of 1-chloro-3,3,3-trifluoropropene, including a reaction in which a halogenated hydrocarbon compound having a carbon number of 3 and represented by a general formula (1) is contacted with a metal catalyst in a gas phase.

$$CF_aCl_{3-a}\text{---}CH_2\text{---}CHF_bCl_{2-b} \qquad (1)$$

In the formula, a is an integer from 0 to 2, b is 1 or 2 when a=0, b is 0 or 1 when a=1, and b is 0 when a=2.

This reaction may be carried out in the presence of at least one kind of fluorocarbon compound selected from 1,3,3,3-tetrafluoropropene, 1,1,3,3-tetrafluoropropene, and 1,1,1,3,3-pentafluoropropane. The fluorocarbon compound may be selected from 1,3,3,3-tetrafluoropropene or 1,1,1,3,3-pentafluoropropane.

In this reaction, 1,1,1,3,3-pentachloropropane may be used instead of the halogenated hydrocarbon compound having a carbon number of 3 and represented by the general formula (1). Alternatively, this reaction may be carried out in the presence of 1,1,1,3,3-pentachloropropane.

The metal catalyst may include at least one kind of metal selected from aluminum, vanadium, chromium, titanium, magnesium, manganese, iron, cobalt, nickel, copper, zirconium, niobium, molybdenum, ruthenium, rhodium, palladium, silver, tin, antimony, zinc, lanthanum, tantalum, and tungsten. The metal catalyst may be an oxide, an oxyhalide, or a halide of the aforementioned metals. The metal catalyst may also include a fluorine atom.

The metal catalyst may be a supported catalyst or a non-supported catalyst. A support for the supported catalyst may be selected from carbon, an oxide of the metal, an oxyhalide of the metal, or a halide of the metal.

The reaction may be conducted at a temperature from 100° C. to 500° C.

In this reaction, hydrogen fluoride may not be substantially supplied. Alternatively, this reaction may be performed in the presence of chlorine.

This reaction may be carried out in the presence of a filler. The filler may be selected from carbon, plastics, ceramics, and a metal.

In this reaction, 1,1,3,3-tetrachloropropene, 1,3-dichloro-3,3-difluoropropene, or 1,3,3-trichloro-3-fluoropropene may be formed in addition to 1-chloro-3,3,3-trifluoropropene.

According to an embodiment of the present invention, it is possible to provide an efficient (and industrially applicable) manufacturing method of 1-chloro-3,3,3-trifluoropropene (1233zd).

DESCRIPTION OF EMBODIMENTS

Hereinafter, each embodiment of the present invention is explained. The embodiments of the present invention should not be interpreted only within the description of the embodiments and examples shown below.

A method according to an embodiment of the present invention includes a reaction in which a halogenated hydrocarbon compound having a carbon number of 3 and represented by a general formula (1) is contacted with a metal catalyst in a gas phase.

$$CF_aCl_{3-a}\text{---}CH_2\text{---}CHF_bCl_{2-b} \qquad (1)$$

In the general formula (1), a is an integer from 0 to 2, b is 1 or 2 when a=0, b is 0 or 1 when a=1, and b is 0 when a=2.

As the halogenated hydrocarbon compound having a carbon number of 3 and represented by the general formula (1), 1,1,3,3-tetrachloro-1-fluoropropane (hereinafter, also referred to as 241fa), 1,1,1,3-tetrachloro-3-fluoropropane (hereinafter, also referred to as 241fb), 1,3,3-trichloro-1,1-difluoropropane (242fa), 1,1,3-trichloro-1,3-difluoropropane (hereinafter, also referred to as 242fb), and 1,1,1-trichloro-3,3-difluoropropane (hereinafter, also referred to as 242fc) are specifically represented. These compounds may be separately used, or a plurality of these compounds may be simultaneously used. Among these compounds, 241fa and 242fa are particularly preferred because 1233zd is preferentially formed. These compounds are known compounds which can be manufactured by the known methods.

The metal catalyst specifically includes at least one kind of metal selected from aluminum, vanadium, chromium, titanium, magnesium, manganese, iron, cobalt, nickel, copper, zirconium, niobium, molybdenum, ruthenium, rhodium, palladium, silver, tin, antimony, zinc, lanthanum, tantalum, and tungsten. It is preferred that the metal catalyst be a compound of the aforementioned metals, and an oxide, an oxyhalide, and a halide of the metals described above are more preferable. The halogen of the halide may be iodine, bromine, chlorine, or fluorine. The metal catalyst is further preferred to be a partially halogenated compound or fully halogenated compound of the aforementioned metals, and a partially fluorinated compound or a fully fluorinated compound of the aforementioned metals is particularly preferred.

The metal catalyst may be a supported catalyst or a non-supported catalyst. The support in the case of the supported catalyst is not particularly limited, and it is preferred to employ carbon as well as an oxide, an oxyhalide (preferably an oxyfluoride), and a halide (preferably a fluoride) of the metals described above, and the like. Among these supports, activated carbon or an oxide, an oxyhalide (an oxyfluoride is particularly preferred), and a halide (a fluoride is particularly preferred) of at least one kind of metal selected from aluminum, chromium, zirconium, and titanium is particularly preferred. In the case of the supported catalyst, the substance supported by the support is the compound of the aforementioned metals and is supported on the support as a halide (e.g., fluoride, chloride, fluorochloride), an oxyhalide (e.g., oxyfluoride, oxychloride, oxyfluorohalide) or a nitrate of the metals, or the like. Such metal compounds may be separately supported, or more than two kinds of metal compounds may be concurrently supported. Among the supported substances, a halide and an oxyhalide of at least one kind of metal selected specifically from aluminum, chromium, zirconium, and titanium are particularly preferred. Chromium nitrate, chromium trichloride, potassium dichromate, titanium trichloride, manganese nitrate, manganese chloride, ferric chloride, nickel nitrate, nickel chloride, cobalt nitrate, cobalt chloride, antimony pentachloride, magnesium chloride, magnesium nitrate, zirconium chloride, zirconium oxychloride, zirconium nitrate, copper(II) chloride, zinc(II) chloride, lanthanum nitrate, tin tetrachloride, and the like can be used as the supported substance.

The metal catalyst is preferred to be used in this reaction after being subjected to a fluorinating treatment. A method of the fluorinating treatment is not particularly limited, and the fluorinating treatment is generally performed by contacting a fluorinating agent such as hydrogen fluoride, a fluorinated hydrocarbon, and a fluorinated and chlorinated hydrocarbon with the metal catalyst. The temperature of the fluorinating treatment is not particularly limited, and the fluorinating treatment is performed at 200° C. or higher, for example. There is no upper limit to the temperature of the fluorinating treatment, and the fluorinating treatment is practically preferred to be conducted at 600° C. or lower. In the present reaction, $Al_2O_3$, $Cr_2O_3$, $Cr_2O_3/Al_2O_3$, $Cr_2O_3/AlF_3$, $Cr_2O_3/C$, $Ti_2O_3$, $Zr_2O_3$, $Zr_2O_3/Ti_2O_3$, $CoCl_2/Cr_2O_3/Al_2O_3$, $NiCl_2/Cr_2O_3/Al_2O_3$, $CoCl_2/AlF_3$, $NiCl_2/AlF_3$, $FeCl_3/C$, $SnCl_4/C$, $TaCl_5/C$, $SbCl_3/C$, $AlCl_3/C$, and $AlF_3/C$, which are subjected to the fluorinating treatment, may be used, for example.

The present reaction may be performed in the presence or in the absence of a filler. Carbon such as activated carbon, heat-resistant plastics, ceramics, and a 0-valent metal such as stainless steel are represented as a filler. Among them, activated carbon is particularly preferred. For instance, this reaction may be carried out in the presence of at least one kind of filler selected from carbon, heat-resistant plastics, and ceramics.

In the present reaction, the reaction temperature is not particularly limited as long as the target compound can be formed. The present reaction may be conducted at 100° C. or higher, a temperature equal to or higher than 150° C. is preferred, a temperature over 200° C. is further preferred, and a temperature equal to or higher than 230° C. is particularly preferred. In addition, the present reaction may be conducted at 500° C. or lower, a temperature equal to or lower than 480° C. is preferred, a temperature equal to or lower than 450° C. is further preferred, and a temperature equal to or lower than 430° C. is particularly preferred. For example, the present reaction may be performed at a temperature from 100° C. to 500° C., a temperature from 150° C. to 480° C. is preferred, a temperature over 200° C. and equal to or lower than 480° C. is further preferred, and a temperature from 230° C. to 430° C. is particularly preferred.

In the present reaction, the reaction pressure is not particularly limited, and the present reaction may be conducted at a reduced pressure, at a normal pressure (an atmospheric pressure), or under pressure. The present reaction may be conducted at 0.01 MPaG to 10 MPaG (i.e., a gage pressure. The same is applied below.), a pressure of 0.01 MPaG to 1 MPaG is preferred, and an atmospheric pressure is more preferred in order to prevent liquefaction of the raw materials and products. It is not economically preferred when the pressure exceeds 10 MPaG because the cost for pressure-proof design of a reaction vessel is increased.

In the case of a gas-phase flow system, productivity is often discussed using a value (second) obtained by dividing a volume A (mL) of a reaction zone by a raw-material supplying rate B (mL/sec), and this value is called a contact time. When a catalyst is added to the reaction zone, the apparent volume (mL) of the catalyst is recognized as A described above. The value of B means "a volume of a raw gas supplied to a reaction vessel every second" and is calculated from a molar number of the raw gas, a pressure, and a temperature under an assumption that the raw gas is an ideal gas.

Determination of the contact time depends on the raw material used in the present reaction, the reaction temperature, the kind of the catalyst, and the like. Thus, it is desirable to appropriately adjust the supply rate of the raw material in view of the raw material, the temperature of the reaction apparatus, and the kind of the catalyst in order to optimize the contact time.

In the present reaction, the contact time may be 0.1 second to 300 seconds, the contact time of 5 seconds to 150 seconds is preferred, and the contact time of 10 seconds to 100 seconds is more preferable. The contact time may be appropriately modified according to the reaction pressure.

In the present reaction, the reaction vessel is not particularly limited, and a reaction vessel suitable for a gas-phase reaction is preferably used. A reaction vessel formed of a material with thermal resistance and acid resistance is preferred, and a reaction vessel formed of stainless steel, Hastelloy™, Monel™, platinum, nickel, carbon, a fluorine resin, or a material lined with these materials is exemplified. However, the material is not limited thereto.

It is preferred to conduct the present reaction in the presence of at least one kind of fluorocarbon compounds selected from 1,3,3,3-tetrafluoropropene (hereinafter, also referred to as 1234ze), 1,1,3,3-tetrafluoropropene (hereinafter, also referred to as 1234zc), and 1,1,1,3,3-pentafluoropropane (hereinafter, also referred to as 245fa) in order to more efficiently manufacture 1-chloro-3,3,3-trifluoropropene (1233zd). The halogenated hydrocarbon compound having a carbon number of 3 and represented by the general formula (1) can be more efficiently converted to 1233zd when the reaction is carried out in the presence of the fluorocarbon compound. In addition, 1233zd can be more efficiently manufactured because the fluorocarbon compound itself is also converted to 1233zd.

In the present reaction, hydrogen fluoride may be supplied to the reaction vessel or may not be supplied. It is preferred not to supply hydrogen fluoride. In an embodiment of the present invention, the halogenated hydrocarbon compound having a carbon number of 3 and represented by the general formula (1) is contacted with the metal catalyst in a gas phase while hydrogen fluoride is not substantially supplied to the reaction vessel.

The fluorocarbon compound may be separately used, or two or more kinds of the fluorocarbon compound may be used. Among them, 245fa and 1234ze are preferred. The compound 1234ze may be a cis form (hereinafter, also referred to as 1234ze(Z)), a trans form (hereinafter, also referred to as 1234ze(E)), or a mixture thereof. These compounds are known compounds capable of being manufactured by the known methods.

When the present reaction is performed in the presence of the fluorocarbon compound, 1,1,1,3,3-pentachloropropane (240fa) may be supplied to the reaction vessel instead of or together with the halogenated hydrocarbon compound having a carbon number of 3 and represented by the general formula (1). This reaction converts 240fa to 1233zd.

The amount of the fluorocarbon compound which is used is not particularly limited. It is preferred to use 5 mol % to 500 mol % of the fluorocarbon compound with respect to the halogenated hydrocarbon compound having a carbon number of 3 and represented by the general formula (1) (in the case of using 240fa together with the halogenated hydrocarbon compound having a carbon number of 3 and represented by the general formula (1), with respect to the total amount of both compounds), and the use of 10 mol % to 300 mol % of the fluorocarbon compound is particularly preferred.

An inert gas such as nitrogen, argon, and helium or an oxidizing gas such as chlorine, oxygen, and air may be supplied to the reaction vessel in view of suppression of side reactions and maintenance and increase of the activity of the metal catalyst. Such a gas may be independently supplied to the reaction vessel or may be supplied to the reaction system together with the halogenated hydrocarbon compound having a carbon number of 3 and represented by the general formula (1) and the fluorocarbon compound. The gas may be separately used or may be a mixed gas. The amount of the gas supplied to the reaction vessel is not limited. It is preferred to use 0.0001 mol % to 200 mol % of the gas with respect to the halogenated hydrocarbon compound having a carbon number of 3 and represented by the general formula (1) (in the case of using 240fa together with the halogenated hydrocarbon compound having a carbon number of 3 and represented by the general formula (1), with respect to the total amount of both compounds), and the use of 0.001 mol % to 100 mol % of the gas is particularly preferred.

The procedure of the method according to the present embodiment is shown. The halogenated hydrocarbon compound having a carbon number of 3 and represented by the general formula (1) and the fluorocarbon compound are introduced to the reaction vessel, and the gas-phase reaction to contact these compounds with the catalyst is carried out under the aforementioned conditions. That is, the halogenated hydrocarbon compound having a carbon number of 3 and represented by the general formula (1) and the fluorocarbon compound in a gas state are contacted with the catalyst. These raw materials are introduced to the reaction vessel via different flow paths or the same flow path. It is preferred that the catalyst be disposed in the reaction vessel in advance. These raw materials are preferred to be in a gas state when introduced to the reaction vessel. If necessary, these raw materials are gasified with a vaporizer and then introduced to the reaction vessel. After that, the reaction is conducted in the reaction vessel under the aforementioned conditions.

A method for purifying the target compound from the reaction products obtained by the present reaction is not particularly limited. If necessary, a removing treatment of a chlorine component or an acid component which may be included in the reaction products may be carried out. Moisture may be also removed by a dehydration treatment and the like, and the dehydration treatment may be conducted with the removing treatment of a chlorine component or an acid component. For example, after the reaction products are allowed to flow through a cooled condenser to be condensed, washed with water and/or an alkaline solution to remove a chlorine component, an acid component, and the like, and dried with a desiccant such as zeolite or activated carbon, the target compound with high purity can be obtained by a distillation operation.

When unreacted raw materials or biproducts other than the target compound are included in the reaction products, they can be independently separated and recovered from the reaction products by a purification operation such as distillation. The separated halogenated hydrocarbon compound having a carbon number of 3 and represented by the general formula (1) and the fluorocarbon compound can be reused as the raw materials of the present reaction and may be also utilized in a variety of usages. Similar to these compounds, the biproducts other than the target compound may be supplied to the present reaction, if necessary, or may be employed in a variety of usages.

According to the present embodiment, 1-chloro-3,3,3-trifluoropropene (1233zd) may be obtained as a cis form (hereinafter, also referred to as 1233zd(Z)), a trans form (hereinafter, also referred to as 1233zd(E)), or a mixture thereof. These cis/trans isomers may be separated from each other by a purification operation such as distillation. The compound 1233zd is useful as a detergent, a coolant, and the like.

In the present reaction, 1,1,3,3-tetrachloropropene (hereinafter, also referred to as 1230za) may be formed. This 1,1,3,3-tetrachloropropene may be utilized in various usages. If necessary, a purification operation is performed to obtain 1230za with high purity. The compound 1230za is useful as a raw material for manufacturing a variety of hydrofluoroolefins (HFO).

In the present reaction, 1,3-dichloro-3,3-difluoropropene (hereinafter, also referred to as 1232zd) may be formed. This 1232zd may be obtained as a cis form (hereinafter, also referred to as 1232zd(Z)), a trans form (hereinafter, also referred to as 1232zd(E)), or a mixture thereof, and these cis/trans isomers may be separated from each other by a purification operation such as distillation. The mixture of the cis/trans isomers of 1232zd or the separated isomers may each be employed in a variety of usages. The compound 1232zd is useful as an operation medium for a thermal cycle.

In the present reaction, 1,3,3-trichloro-3-fluoropropene (hereinafter, also referred to as 1231zd) may be formed. This 1231zd may be obtained as a cis form (hereinafter, also referred to as 1231zd(Z)), a trans form (hereinafter, also referred to as 1231zd(E)), or a mixture thereof, and these cis/trans isomers may be separated from each other by a purification operation such as distillation. The mixture of the cis/trans isomers of 1231zd or the separated isomers may each be employed in a variety of usages. The compound 1231zd is one of hydrofluoroolefins (HFO) with a low global warming potential coefficient (GWP) and is expected as an alternative fluorocarbon.

EXAMPLES

Hereinafter, an embodiment according to the present invention is explained in detail using Examples. The embodiments of the present invention are not limited to the Examples.

In the present specification, the term FID % means an area percentage of a chromatogram obtained by a gas chromatography analysis using an FID as a detector.

Preparation Example 1

Preparation of Fluorinated Activated Alumina

Activated alumina (300 g, KHS-46 manufactured by Sumitomo Chemical Co., Ltd, particle size of 4 to 6 mm and a specific surface area of 155 $m^2/g$) was weighted out, and powder adhered on its surface was washed out with water. To the washed alumina was slowly added 1150 g of 10 wt % hydrofluoric acid, and the mixture was stirred and then kept standing for 4 hours. After washing with water, the activated alumina was filtered, dried at a normal temperature overnight, and then dried in an electric furnace at 200° C. for 2 hours. Into a reaction tube made of stainless steel (SUS 316) and having an internal diameter of 1 inch and a length of 40 cm was added 150 mL of the dried alumina, and the temperature of the reaction tube was increased to 200° C. in the electric furnace while allowing nitrogen to flow therethrough at a flow rate of 150 cc/sec and then allowing hydrogen fluoride to flow therethrough at a flow rate of 0.1 g/min together with nitrogen. Since the temperature increases as the hydrogen fluoride treatment proceeds, the flow rates of nitrogen and hydrogen fluoride were adjusted to prevent the inner temperature from exceeding 400° C. When the heat generation was completed, the flow rate of nitrogen was dropped to 30 cc/sec, the set temperature of the electric furnace was increased by 50° C. every 30 minutes to a final temperature of 400° C., and then this state was maintained for two hours. The activated alumina subjected to the fluorinating treatment (hereinafter, also referred to as a catalyst 1) was prepared in this way.

Preparation Example 2

Preparation of Fluorinated Chromium-Supporting Alumina Catalyst

To an Erlenmeyer flask was added a 20 wt % aqueous solution of chromium chloride, and 100 mL of the activated alumina subjected to the fluorinating treatment and prepared in the Preparation Example 1 was soaked and kept therein for 3 hours. This alumina was filtered and dried at 70° C. under a reduced pressure using a rotary evaporator. Into a cylinder-shaped reaction tube made of stainless steel (SUS 316), having an internal diameter of 1 inch and a length of 40 cm, and equipped with an electric furnace was charged with 100 mL of this chromium-supporting alumina, and the temperature was increased to 200° C. while allowing nitrogen to flow therethrough. When no more water outflow was observed, nitrogen gas and hydrogen fluoride were simultaneously supplied at flow rates of 150 cc/sec and 0.1 g/sec, respectively, and the flow rates of nitrogen and hydrogen fluoride were adjusted so that the inner temperature does not exceed 400° C. When the hot spot caused by the fluorination of the charged chromium-supporting alumina reached an outlet terminal of the reaction tube, the flow rate of nitrogen was reduced to 30 cc/sec, the set temperature of the electric furnace was increased by 50° C. every 30 minutes to the final temperature of 400° C., and then this state was maintained for 2 hours. The chromium-supporting alumina subjected to the fluorinating treatment (hereinafter, also referred to as a catalyst 2) was prepared in this way.

Preparation Example 3

Preparation of Fluorinated Chromium-Supporting Activated Carbon

To an Erlenmeyer flask was added a 20 wt % aqueous solution of chromium chloride, and 100 mL of activated carbon was soaked and maintained therein for 3 hours. This activated carbon was filtered and dried at 70° C. under a reduced pressure using a rotary evaporator. Into a cylinder-shaped reaction tube made of stainless steel (SUS 316), having an internal diameter of 1 inch and a length of 40 cm, and equipped with an electric furnace was charged with 100 mL of the obtained chromium-supporting activated carbon, and the temperature was increased to 200° C. while allowing nitrogen to flow therethrough. When no more water outflow was observed, nitrogen gas and hydrogen fluoride were simultaneously supplied at flow rates of 150 cc/sec and 0.1 g/sec, respectively, and the flow rates of nitrogen and hydrogen fluoride were adjusted so that the inner temperature does not exceed 400° C. When the hot spot caused by the fluorination of the charged chromium-supporting activated carbon reached an outlet terminal of the reaction tube, the flow rate of nitrogen was reduced to 30 cc/sec, the set temperature of the electric furnace was increased by 50° C. every 30 minutes to the final temperature of 400° C., and then this state was maintained for 2 hours. The chromium-supporting activated carbon subjected to the fluorinating treatment (hereinafter, also referred to as a catalyst 3) was prepared in this way.

Example 1-1

Into a cylinder-shaped reaction tube made of stainless steel (SUS 316), having an internal diameter of 1 inch and a length 40 cm, and equipped with an electric furnace was charged with 50 mL of the catalyst prepared in the Preparation Example 1, and the internal temperature of the reaction tube was increased to 300° C. while allowing nitrogen gas to flow therethrough at a flow rate of approximately 30 cc/min. After that, the supply of nitrogen was stopped, and vaporized 1,3,3-trichloro-1,1-difluoropropane (242fa, purity of 96.7 FID %, the same is applied below) and 1,1,1,3,3-pentafluoropropane (245fa, purity of 99.9 FID %, the same is applied below) were introduced into the reaction tube (molar ratio of 242fa/245fa=1/1, contact time of 60 seconds). When the flow rate became stable, 500 mL of a water trap cooled with ice water was disposed at an outlet of the reaction tube, by which the organic substances were recovered and a by-produced acid component was absorbed for approximately 100 minutes. The gas passing through the water trap was recovered by a dry ice trap disposed next to the water trap, and the recovered materials in the water trap and the dry ice trap were mixed. The composition of the organic substances obtained by removing an acid from the recovered materials was analyzed with a gas chromatography. The result is shown in Table 1.

Examples 1-2 to 1-4

The same operations were carried out as those of the Example 1-1 except that the internal temperatures of the reaction tubes were respectively set to be 200° C., 250° C., and 350° C.

Example 2-1

The same operations were carried out as those of the Example 1-1 except that 1,1,3,3-tetrachloro-1-fluoropropane (241fa, purity of 98.2 FID %, the same is applied below) was introduced instead of 1,3,3-trichloro-1,1-difluoropropane (242fa).

Examples 2-2 to 2-4

The same operations were carried out as those of the Example 2-1 except that the internal temperatures of the reaction tubes were respectively set to be 200° C., 250° C., and 350° C.

Example 3-1

The same operations were carried out as those of the Example 1-1 except that 1,1,1,3-tetrafluoropropene (1234ze, purity of 99.9 FID %, the same is applied below) was introduced instead of 1,1,1,3,3-pentafluoropropane (245fa).

Example 3-2

The same operations were carried out as those of the Example 1-1 except that 100 mL of the catalyst prepared in the Preparation Example 1 was charged, 1,1,1,3-tetrafluoropropene (1234ze) was introduced instead of 1,1,1,3,3-pentafluoropropane (245fa), and chlorine was introduced (molar ratio of 242fa/1234ze/chlorine=1/0.5/0.02, contact time of 60 seconds).

The obtained crude product, 800 g, was separated and purified with a normal-pressure distillation tower in which 10 stages of Heli Packs No. 2 were charged to obtain a 95 g of an initial fraction (the temperature of the tower top was 5-19° C., 17.0 FID % of 1234ze, 6.0 FID % of 245fa, and 77.0 FID % of 1233zd(E)), 600 g of a second fraction (the temperature of the tower top was 19.0-19.2° C., 99.9 FID % of 1233zd(E)), 60 g of a third fraction (the temperature of the tower top was 39.0 to 39.2° C., 99.5 FID % of 1233zd(Z)), and 40 g of residue mainly including 1230za.

Next, the same operations as those of the Example 1-1 were performed except that the aforementioned initial fraction (a ratio of 242fa/amount of the introduced initial fraction=1/4.3, a contact time of 60 seconds) was introduced instead of 245fa.

Example 3-3

The same operations were carried out as those of the Example 1-1 except that 1,1,1,3,3-pentafluoropropane (245fa) was not introduced.

Example 3-4

The same operations were carried out as those of the Example 1-1 except that 1,1,3,3-tetrachloro-1-fluoropropane (241fa) was introduced instead of 1,3,3-trichloro-1,1-difluoropropane (242fa) and 1,1,1,3,3-pentafluoropropane (245fa) was not introduced.

Example 3-5

The same operations were carried out as those of the Example 1-1 except that 1,1,3,3-tetrachloro-1-fluoropropane (241fa) was introduced instead of 1,3,3-trichloro-1,1-difluoropropane (242fa) and 1,3,3,3-tetrafluoropropene (1234ze) was introduced instead of 1,1,1,3,3-pentafluoropropane (245fa).

Example 4-1

The same operations were carried out as those of the Example 1-1 except that 50 mL of the catalyst prepared in the Preparation Example 2 was charged instead of the catalyst prepared in the Preparation Example 1.

Example 4-2

The same operations were carried out as those of the Example 1-1 except that 50 mL of the catalyst prepared in the Preparation Example 3 was charged instead of the catalyst prepared in the Preparation Example 1.

Example 5-1

The same operations as those of the Example 1-1 were performed except that 242fa and 1,1,3,3-tetrachloro-1-fluoropropane (241fa) were introduced (molar ratio of 241fa/242fa/245fa=1.1/1.5/1.8, a contact time of 60 seconds) instead of 1,3,3-trichloro-1,1-difluoropropane (242fa).

Referential Example 1

The same operations as those of the Example 1-1 were performed except that 50 mL of activated carbon was charged instead of the catalyst prepared in the Preparation Example, 1, 1,1,1,3,3-pentafluoropropane (245fa) was not introduced, and the internal temperature of the reaction tube was set to 250° C.

Referential Example 2

The same operations as those of the Example 1-1 were performed except that 50 mL of activated carbon was charged instead of the catalyst prepared in the Preparation Example 1, 1,1,3,3-tetrachloro-1-fluoropropane (241fa) was introduced instead of 1,3,3-trichloro-1,1-difluoropropane (242fa), and the internal temperature of the reaction tube was set to 200° C.

The results of the Examples and the Referential Examples are summarized in Table 1. In Table 1, "-" means that no substance was detected.

|  | Samples | Raw Material 1 | Raw Material 2 | Catalyst | Reaction Temperature (°C.) | Organic Composition (FID %) | | |
|---|---|---|---|---|---|---|---|---|
|  |  |  |  |  |  | 1234zeE | 245fa | 1234zeZ |
| Examples | 1-1 | 242fa | 245fa | 1 | 300 | 1.3 | 0.7 | 0.3 |
|  | 1-2 | 242fa | 245fa | 1 | 200 | 6.1 | 17 | 1 |
|  | 1-3 | 242fa | 245fa | 1 | 250 | 4 | 10.7 | 0.8 |
|  | 1-4 | 242fa | 245fa | 1 | 350 | 0.9 | 0.5 | 0.1 |
|  | 2-1 | 241fa | 245fa | 1 | 300 | 2.8 | 1.7 | 0.5 |
|  | 2-2 | 241fa | 245fa | 1 | 200 | 9 | 15 | 1 |
|  | 2-3 | 241fa | 245fa | 1 | 250 | 6.8 | 13.6 | 1.5 |
|  | 2-4 | 241fa | 245fa | 1 | 350 | 1.5 | 1 | 0.1 |
|  | 3-1 | 242fa | 1234ze | 1 | 300 | 4 | 0.9 | 0.7 |
|  | 3-2 | 242fa | Initial fraction | 1 | 300 | 0.6 | 0.2 | 0.1 |
|  | 3-3 | 242fa | — | 1 | 300 | — | — | — |
|  | 3-4 | 241fa | — | 1 | 300 | — | — | — |
|  | 3-5 | 241fa | 1234ze | 1 | 300 | 7.5 | 0.1 | 1.7 |
|  | 4-1 | 242fa | 245fa | 2 | 300 | 0.5 | 10 | 0.1 |
|  | 4-2 | 242fa | 245fa | 3 | 300 | 0.4 | 10.3 | 0.1 |
|  | 5-1 | 242fa + 241fa | 245fa | 1 | 300 | 2.1 | 1.2 | 0.4 |
| Referential Example | 1 | 242fa | — | — | 250 | — | — | — |
|  | 2 | 241fa | — | — | 200 | — | — | — |

|  | Samples | Organic Composition (FID %) | | | | | |
|---|---|---|---|---|---|---|---|
|  |  | 1233zdE | 1233zdZ | 1232zd | 1231zd | 1230za | Raw Material1 |
| Examples | 1-1 | 83.1 | 10 | 1.1 | <0.1 | 1.9 | <0.1 |
|  | 1-2 | 20.5 | 2.6 | 8.1 | <0.1 | 17 | 26.1 |
|  | 1-3 | 71.2 | 7.1 | 1.2 | <0.1 | 3.4 | <0.1 |
|  | 1-4 | 84.2 | 11 | 1 | <0.1 | 1.1 | <0.1 |
|  | 2-1 | 76.9 | 9 | 3.5 | 0.3 | 4.2 | <0.1 |
|  | 2-2 | 19.5 | 3 | 1 | 1 | 27 | 22 |
|  | 2-3 | 63.1 | 5.9 | 2 | 0.4 | 5.8 | 0.2 |
|  | 2-4 | 82.1 | 10 | 2.3 | 0.1 | 1.5 | <0.1 |
|  | 3-1 | 82.7 | 9.5 | 0.4 | <0.1 | 0.9 | <0.1 |
|  | 3-2 | 88.5 | 10 | 0.2 | <0.1 | 0.1 | <0.1 |
|  | 3-3 | 56.1 | 6.1 | 4.2 | <0.1 | 30.3 | 2.5 |
|  | 3-4 | 31.3 | 3.2 | 2.1 | 0.1 | 63.2 | <0.1 |
|  | 3-5 | 71.3 | 9.1 | 1.9 | <0.1 | 6.5 | <0.1 |
|  | 4-1 | 67.9 | 8.5 | 5.6 | <0.1 | 2.9 | 3 |
|  | 4-2 | 69.1 | 11.5 | 4.4 | <0.1 | 1.3 | 2.1 |
|  | 5-1 | 80.1 | 10 | 2.2 | 0.1 | 3.3 | <0.1 |
| Referential Example | 1 | 0.8 | 0.2 | 93 | <0.1 | 2.3 | 2.1 |
|  | 2 | <0.1 | <0.1 | 9.1 | 48 | 20.2 | 12 |

As is clearly revealed from Table 1, it was proven that implementation of the method according to the present embodiment makes it possible to highly selectively manufacture 1233zd in a high yield from the halogenated hydrocarbon compound having a carbon number of 3 and represented by the general formula (1).

INDUSTRIAL APPLICABILITY

The use of a halogenated hydrocarbon compound, which is readily available and has a carbon number of 3, as a raw material allows a chlorofluoropropene having a low GWP and applicable in a variety of usages to be manufactured in an industrial scale.

Hereinafter, examples of other embodiments are additionally noted.

1. A method for manufacturing 1,1,3,3-tetrachloropropene (1230za), the method including contacting a halogenated hydrocarbon compound having a carbon number of 3 and represented by a general formula (1) with a metal catalyst in a gas phase.

$$CF_aCl_{3-a}-CH_2-CHF_bCl_{2-b} \quad (1)$$

In the formula, a is an integer from 0 to 2, b is an integer from 0 to 2 when a=0, b is an integer from 0 to 1 when a=1, and b is 0 when a=2.

2. The method described in 1, where at least one kind of fluorocarbon compound selected from 1,3,3,3-tetrafluoropropene (1234ze), 1,1,3,3-tetrafluoropropene (1234zc), and 1,1,1,3,3-pentafluoropropane (245fa) is supplied in the reaction.

3. The method described in 1 or 2, where the halogenated hydrocarbon compound having a carbon number of 3 and represented by the general formula (1) is at least one kind of compound selected from 1,1,3,3-tetrachloro-1-fluoropropane (241fa), 1,1,1,3-tetrachloro-3-fluoropropane (241fb), 1,3,3-trichloro-1,1-difluoropropane (242fa), 1,1,3-trichloro-1,3-difluoropropane (242fb), and 1,1,1-trichloro-3,3-difluoropropane (242fc).

4. The method described in 2 or 3, where the fluorocarbon compound is 1,3,3,3-tetrafluoropropene (1234ze) or 1,1,1,3,3-pentafluoropropane (245fa).

5. The method described in any of 1 to 4, where the metal catalyst includes at least one kind of metal selected from aluminum, vanadium, chromium, titanium, magnesium, manganese, iron, cobalt, nickel, copper, zirconium, niobium, molybdenum, ruthenium, rhodium, palladium, silver, tin, antimony, zinc, lanthanum, tantalum, and tungsten.

6. The method described in 5, where the metal catalyst is an oxide of the metal, an oxyhalide of the metal, or a halide of the metal.

7. The method described in 5 or 6,
where the metal catalyst is a supported catalyst or a non-supported catalyst, and
a support of the supported catalyst is carbon, an oxide of the metal, an oxyhalide of the metal, or a halide of the metal.

8. The method described in any of 1 to 7, where the metal catalyst includes at least a fluorine atom.

9. The method described in any of 1 to 8, where a reaction temperature is 100° C. to 500° C. in the reaction.

10. The method described in any of 1 to 9, where hydrogen fluoride is not substantially supplied in the reaction.

11. The method described in any of 1 to 10, where the reaction is carried out in the presence of chlorine.

12. The method described in any of 1 to 11, where the reaction is carried out in the absence of a metal catalyst.

13. The method described in any of 1 to 12, where the reaction is carried out in the presence of a filler.

14. The method described in 13, where a material of the filler is at least one kind of material selected from carbon, plastics, ceramics, and a metal.

15. The method described in any of 1 to 14, where 1-chloro-3,3,3-trifluoropropene (1233zd), 1,3-dichloro-3,3-difluoropropene (1232zd), or 1,3,3-trichloro-3-fluoropropene (1231zd) is formed in addition to 1,1,3,3-tetrachloropropene (1230za) in the reaction.

What is claimed is:

1. A method for manufacturing 1-chloro-3,3,3-trifluoropropene, the method comprising contacting a halogenated hydrocarbon compound and represented by a general formula (1) with a metal catalyst in a gas phase:

$$CF_aCl_{3-a}-CH_2-CHF_bCl_{2-b} \qquad (1),$$

wherein the reaction is carried out in the presence of at least one fluorocarbon compound selected from the group consisting of 1,3,3,3-tetrafluoropropene, 1,1,3,3-tetrafluoropropene, and 1,1,1,3,3-pentafluoropropane,
wherein hydrogen fluoride is not supplied in the reaction,
wherein a temperature of the reaction is equal to or higher than 230° C., and
wherein, in the formula, a is an integer from 0 to 2, b is 1 or 2 when a=0, b is 0 or 1 when a=1, and b is 0 when a=2.

2. The method according to claim 1, wherein the reaction is carried out in the presence of 1,1,1,3,3-pentachloropropane.

3. The method according to claim 1, wherein the fluorocarbon compound is 1,3,3,3-tetrafluoropropene or 1,1,1,3,3-pentafluoropropane.

4. The method according to claim 1, wherein the metal catalyst includes at least one metal selected from the group consisting of aluminum, vanadium, chromium, titanium, magnesium, manganese, iron, cobalt, nickel, copper, zirconium, niobium, molybdenum, ruthenium, rhodium, palladium, silver, tin, antimony, zinc, lanthanum, tantalum, and tungsten.

5. The method according to claim 4, wherein the metal catalyst is an oxide of the metal, an oxyhalide of the metal, or a halide of the metal.

6. The method according to claim 4,
wherein the metal catalyst is a supported catalyst or a non-supported catalyst, and
a support of the supported catalyst is carbon, an oxide of the metal, an oxyhalide of the metal, or a halide of the metal.

7. The method according to claim 1, wherein the metal catalyst includes at least a fluorine atom.

8. The method according to claim 1, wherein the reaction is carried out in the presence of chlorine.

9. The method according to claim 1, wherein the reaction is carried out in the presence of a filler.

10. The method according to claim 9, wherein the filler is at least one material selected from the group consisting of carbon, plastics, ceramics, and a metal.

11. The method according to claim 1, wherein 1,1,3,3-tetrachloropropene, 1,3-dichloro-3,3-difluoropropene, or 1,3,3-trichloro-3-fluoropropene is formed in addition to 1-chloro-3,3,3-trifluoropropene in the reaction.

* * * * *